United States Patent [19]

Tso

[11] Patent Number: 5,840,688
[45] Date of Patent: Nov. 24, 1998

[54] EATING SUPPRESSANT PEPTIDES

[75] Inventor: Patrick Tso, Shreveport, La.

[73] Assignee: Research Corporation Technologies, Inc., Tucson, Ariz.

[21] Appl. No.: 408,858

[22] Filed: Mar. 22, 1995

Related U.S. Application Data

[63] Continuation-in-part of Ser. No. 216,537, Mar. 22, 1994, abandoned.
[51] Int. Cl.[6] .......................... A61K 38/06; A61K 38/07; A61K 38/08; A61K 38/10
[52] U.S. Cl. ............................ 514/12; 426/648; 426/656; 514/13; 514/14; 514/15; 514/16; 514/17; 514/18; 530/324; 530/325; 530/326; 530/327; 530/328; 530/329; 530/330; 530/331
[58] Field of Search .................................. 514/12, 13, 14, 514/15, 16, 17, 18; 530/324, 326, 327, 328, 329, 330, 331, 359

[56] References Cited

U.S. PATENT DOCUMENTS

| | | | |
|---|---|---|---|
| 3,832,465 | 8/1974 | Ghadimi | 424/177 |
| 5,013,722 | 5/1991 | Danho et al. | 514/16 |

FOREIGN PATENT DOCUMENTS

| | | |
|---|---|---|
| WO 92/00753 | 1/1992 | WIPO . |
| WO 94/27629 | 12/1994 | WIPO . |

OTHER PUBLICATIONS

Boguski et al. (1984) "Rat Apolipoprotein A–IV Contains 13 Tandem Reptitions of a 22–Amino Acid Segment with Amphipathic Helical Potential," *Proc. Natl. Acad. Sci. USA* 81:5021–5025.
Boguski et al. (1986) "Evolution of Apolipoproteins," *J. Biol. Chem.* 261(14):6398–6407.
Fujimoto et al. (1992) "Increased Apolipoprotein A–IV in Rat Mesenteric Lymph After Lipid Meal Acts as a Physiological Signal for Satiation," *Am. J. Physiol.*, pp. G1002–G1006.
Fujimoto et al. (1986) "Anorexia Induced in Rat by D–Glucosamine Deoxidized at C–1," *Am. J. Physiol.*, pp. R481–R491.
Fujimoto et al. (1993) "Suppression of Food Intake by Apolipoprotein A–IV is Mediated Through the Central Nervous System in Rats," *J. Clin. Invest.* 91:1830–1833.
Fujimoto et al. (1993) "Effect of Intravenous Administration of Apolipoprotein A–IV on Patterns of Feeding , Drinking, and Ambulatory Activity of Rats," *Brain Research* 608:233–237.
Gordon et al. (1984) "Biosynthesis of Human Preaoplipoprotein A–IV," *J. Biol. Chem.* 259(1):468–474.
Haddad et al. (1986) "Linkage, Evolution, and Expression of the Rat Apolipoprotein A–I, C–III, and A–IV Genes," *J. Biol. Chem.* 261(28):13268–13277.
Karathanasis et al. (1986) "Structure, Evolution and Polymorphisms of the Human Apolipoprotein A4 Gene (APOA4)," *Proc. Natl. Acad. Sci. USA* 83:8457–8461.

(List continued on next page.)

*Primary Examiner*—Jeffrey E. Russel
*Attorney, Agent, or Firm*—Scully, Scott, Murphy & Presser

[57] ABSTRACT

Peptides corresponding to specific portions of the apolipoprotein A-IV (apo A-IV) are provided. Most of the peptides correspond to the amino terminal region of apo A-IV. In addition, those peptides corresponding to the amino terminal portion of apo A-IV substantially correspond to a fundamental repeat unit of twenty two amino acids comprising:

DYFTQLSNNAKEAVEQLQKTDV SEQ ID NO:88 as well as homologs and analogs thereof. The peptides have eating suppressant properties when administered centrally or peripherally. The peptides may be used in compositions and methods for suppressing the appetite and controlling food intake.

18 Claims, 7 Drawing Sheets

OTHER PUBLICATIONS

Morley et al. (1987) "An Investigation of Tolerance to the Actions of Leptogenic and Anorexigenic Drugs in Mice," *Life Sciences* 41:2157–2165.

Shargill et al. (1991) "Enterostatin Suppresses Food Intake Following Injection Into the Third Ventricle of Rats," *Brain Research* 544:137–140.

Tso et al. (1991) "The Absorption and Transport of Lipids by the Small Intestine," *Brain Research Bulletin* 27:477–482.

Yang et al. (1989) "The Primary Structure of Human Apolipoprotein A–IV" *Biochimica et Biophysica Acta.* *1002*:231–237.

Fujimoto et al. (1992) "Increased Apolipoprotein A–IV in Rats Mesenteric Lymph after Lipid Meal Acts as a Physiological Signal for Satiation" *Amer. J. Physiol.* 6(1):G1002–1006.

Miyoshi et al. (1978) "Deprotection of Protected Peptides" *Chemical Abstracts* 88(11):abstract No. 74543t.

Rexova et al. (1964) "Chemical Characterisation of Some Low Molecular Components of Honeybee Poison" *Chemical Abstracts* 60(12):abstract No. 14749d.

Van Vunakis et al. (1964) "Structural Studies on Pepsinogen and Pepsin: An Immunologic Approach" *Chemical Abstracts* 60(4):abstract No. 4407h.

Dimarchie et al. "Solid Phase Synthesis of the . . . Acid" Int. J. Pept. Protein Res. (1982) vol. 19, No. 3 pp. 270–279.

EATING SUPPRESSANT PEPTIDES

This is a continuation-in-part of U.S. patent application Ser. No. 08/216,537, which was filed on Mar. 22, 1994 now abandoned.

The invention described herein was made in the course of and under grants from the National Institutes of Health (Nos. NIH DK-32288 and DK-01575) and is therefore subject to the rights of the U.S. government therein.

TECHNICAL FIELD

The present invention relates to protein and peptide chemistry. In particular, it relates to the discovery and isolation of novel peptides whose sequences coincide to regions of the protein, apolipoprotein A-IV. The invention is also directed to the use of these novel peptides in the suppression of appetite and food intake.

BACKGROUND OF THE INVENTION

Apolipoproteins are the protein components of lipid-protein complexes (lipoproteins) found in the plasma. In addition to the ability to bind lipids, individual apolipoproteins have unique functions such as the formation of specific associations with lipoprotein particles of distinct density classes. Some apolipoproteins act as ligands controlling the interaction of lipoproteins with cell surface receptors. Apolipoproteins also function as cofactors for essential enzymes in lipid metabolism. (Boguski et al., J. Biol. Chem., 261: 6398–6407, 1986).

In humans, there exist numerous apolipoproteins. Expression of these different apolipoproteins is under the control of developmental, hormonal, dietary and tissue specific regulation. (See e.g., Boguski et al., J. Biol. Chem., 261: 6398–6407, 1986). The amino acid sequences of rat and human apo A-I, apo C-III and apo A-IV share considerable regions of homology. Nucleotide sequences of the exons in the genes coding for these three apolipoproteins in rat and human are significantly homologous and are located on chromosome eleven in both species. (See e.g., Haddad et al., J. Biol. Chem. 261: 13268–13277, 1986, Li et al., J. Lipid Res. 29: 245–271, (1988).

The relative size, direction of transcription and intron-exon organization of the apo A-I, apo C-III and apo A-IV genes in rat and human are also similar. Two introns in particular found in the apo A-I, apo C-III, and apo A-IV genes of both species interrupt coding regions at similar positions. Further, the points of interruption define specific amino acid domains involved in secretion (signal peptide) and in lipid binding (amphipathic region) of the apo A-I, apo C-III and apo A-IV proteins. Id.

The nucleotide sequences located upstream of the transcriptional start sites of the rat apo A-I, apo C-III and apo A-IV genes are significantly homologous to the corresponding nucleotide sequences in human. Most likely, expression of these genes is regulated by cis-acting DNA elements located 5' to their respective promoter sequences and is regulated similarly in rat and human. Id.

The complete amino acid sequence of apo A-IV has been reported for mouse (Williams et al., Mol. and Cell. Biol. 6(11): 3807–3814, 1986), rat (Haddad et al., J. Biol, Chem. 261: 13268–13277, 1986), and human (Karathanasis et al., Proc. Natl. Acad. Sci. U.S.A. 83: 8457–8461, 1986). Apo A-IV is initially synthesized as a larger precursor with a 20 amino acid signal peptide sequence. (Gordon et al., J. Biol. Chem. 259:468–471, 1984). The amino acid sequence of the apo A-IV signal peptide is extremely conserved among mouse, rat and human. A comparison of the amino acid sequence of the signal peptide of rat and human apo A-IV reveals that 15 out of 20 amino acids are identical. The signal sequences of mouse and human apo A-IV are identical in sixteen out of twenty amino acids with one gap introduced into the mouse sequence to align for maximum homology. When the rat and human amino acid sequences for the entire apo A-IV precursor are compared, a sequence homology of 63% is revealed. Mouse and human apo A-IV precursor proteins have an amino acid sequence homology of 61%.

Excluding their respective signal peptides, the apolipoproteins are largely composed of multiple copies of lipid-binding sequences that have undergone varying degrees of divergence. For example, apolipoproteins A-I, A-IV, and E are largely composed of multiple, tandemly repeated sequences coding for amphipathic docosapeptides. (See e.g., Boguski et al., J. Biol. Chem. 261: 6398–6397, 1984). The fundamental repeat unit in the apolipoproteins is eleven amino acids or thirty three nucleotides. A repeat unit of twenty two amino acids or sixty six nucleotides appears to be the more common evolutionary unit and may also be a functional unit. Id. The repeat unit in rat comprises the following amino acid sequence:DYFTQLSNNAK EAVEQLQKTDV SEQ ID NO:88 and analogs thereof. The tandemly repeated docosapeptides in human apo A-IV are also not exact duplications. Most amino acid substitutions, however, are conservative i.e., substituted amino acids have similar physical chemical properties. In the case of nonconservative substitutions which appear in some of the apo A-IV repeat units, approximately half are substituted by the small, neutral amino acids glycine, serine, or threonine. (Boguski et al., Proc. Nat. Acad. Sci. U.S.A., 81:5021–5025, 1984).

Apolipoprotein A-IV (apo A-IV) is a 46,000-Da polypeptide associated with lipoproteins and in human, is produced exclusively by the small intestine. (Swaney et al., Biochemistry 6: 271–279, 1977; Tso, P., Adv. Lipid Res., 21:143–186, 1985; Sherman et al., Gastroenterology 95: 394–401, 1988). The twenty amino acid signal peptide is cleaved during secretion of apo A-IV by the small intestinal epithelial cells. (Gordon et al., J. Biol. Chem., 257: 8418–8423, 1982). Also in humans, apo A-IV is abundantly present in triglyceride-rich lipoproteins as well as the d>1.21 g/ml-fraction of the plasma. (See e.g., Gordon et al., J. Biol. Chem. 259:468–474, 1984).

Although apo A-IV was discovered more than 18 years ago (Swaney et al., Biochemistry 16:271–278, 1977) and rat apo A-IV CDNA sequence was reported by Boguski et al., (Proc. Nat. Acad. Sci. U.S.A., 81: 5021–5025, 1984), its physiological function has not been well understood. Recently, however, it has been demonstrated that apo A-IV synthesis by the small intestine increases markedly after the ingestion of lipid with the resultant effect being a marked increase in apo A-IV output in mesenteric lymph. (Krause et al., L. Lipid Res., 22: 610–619, 1981; Hayashi et al., L. Lipid Res., 31:1613–1625, 1990). Because intestinal synthesis and secretion of apo A-IV increases after triacylglycerol feeding, it is thought that apo A-IV may be involved in the biogenesis and/or metabolism of intestinal triglyceride-rich lipoproteins. (Gordon et al., Biochemistry, 259:468–474, 1984). It has also been demonstrated that this increase in biosynthesis and secretion of apo A-IV by the small intestine after fat feeding is triggered by the formation and secretion of intestinal chylomicrons. (Hayashi et al., L. Lipid Res.. 31:1613–1625, 1990; Apfelbaum et al., Am. J. Physiol. 252: G662–G666, 1987). Further, it has been shown that the apo A-IV appearing in mesenteric lymph after a lipid meal suppresses food intake, thus suggesting that apo A-IV may also act as a satiety factor that circulates in the blood after fat feeding. (Fujimoto et al., Am. J. Physiol. 262:G1002–G1006, 1992).

Feeding behavior is influenced by many circulating chemical factors, and chemosensitive monitoring systems for these factors exist both in the central nervous system and in peripheral organs (Bray et al., Vitam. Horm., 45:1–125, 1989, Oomura et al., J. Auto. Nerv. Sys.,10:359–372, 1984, Novin et al., Diabetologia, 20: 331–336, 1981). Recently, it has been shown that when apo A-IV is administered centrally in male Sprague Dawley rats, food intake is significantly suppressed in a dose-dependent manner. (Fujimoto et al., J. Clin. Invest. 4: 1830–1833, 1993). In addition, apo A-IV is more than 50 fold more potent when administered centrally than when administered peripherally. These data suggest the possible existence of specific receptors in the central nervous system which respond to apo A-IV. Id.

That apo A-IV suppresses food intake via the central nervous system is further supported by data which shows that goat anti-rat apo A-IV serum infused into the third ventricle in rats fed ad libitum elicited feeding in all animals tested. In contrast, the administration of anti-rat apo A-I serum or saline into the third ventricle fails to elicit feeding. (Fujimoto et al., J. Clin. Invest. 4: 1830–1833, 1993). One explanation for these observations is that administration of apo A-IV antiserum in the third ventricle leads to a removal of endogenous apo A-IV. Id.

Approximately 25% of the U.S. population is considered obese (body weight more than 20% over ideal) and 13% of the population is considered morbidly obese. (Marketletter, p. 18, IMSWORLD publ. Ltd., Oct. 1, 1990). Morbidly obese individuals are those in a life threatening situation due to their obesity. Further, the National Association of Anorexia Nervosa and Associated Eating Disorders estimates that eight million U.S. citizens suffering from eating disorders often go back and forth between anorexia and bulimia. Presently, effective drugs are not available for treating individuals suffering from eating disorders resulting in obesity or psychological conditions.

The mainstays of the anorexiant market are prescription amphetamines, their derivatives and over-the-counter phenylpropanolamine and its derivatives. These drugs have several shortcomings. For example, amphetamines have the drawback of being euphoretics with mind altering properties. Phenylpropanolamine and its derivatives have unwanted sedating side effects. Moreover, once these drugs and other antidepressants are no longer administered, weight loss is often not maintained.

Several peptides have been proposed as affecting eating behavior and therefore, possible anorectic agents. Glucagon, cholecystokinin, anorectin (a fragment of growth hormone), corticotropin releasing hormone, enterostatin, calcitonin, neurotensin, bombesin and cyclo-HisPro have all been shown to decrease food intake in animal studies. Many of these peptides, however, have serious, undesirable side effects or other complications such as lack of potency, effects on behavior which produce indirect loss of eating and large size which results in immunogenicity and/or lack of access to appropriate brain areas.

Thus, there is a great need for a safe, effective appetite suppressant with little or no complications and side effects.

SUMMARY OF THE INVENTION

The present invention provides a method and means for suppressing appetite and inhibiting food intake. In accordance with the present invention, a number of novel eating suppressant peptides, derived from apolipoprotein A-IV have been made by solid phase peptide synthesis. These peptides possess appetite suppressant properties which when administered orally or intravenously, can be used to inhibit food intake in an individual's diet. Because of their relatively small size, the peptides of the present invention should be able to pass through the blood brain barrier if necessary. Since the peptides comprise specific portions of the native apo A-IV protein, there should be no immunogenicity problems associated with their administration to humans. In addition, administering the peptides of the present invention may allow for a more specific satiation signal.

The peptides of the present invention correspond to specific areas of the apolipoprotein A-IV molecule and comprise at least a fragment of a fourteen amino acid sequence derived from the amino terminal portion of the mature apolipoprotein A-IV, which has been identified in accordance with the present invention to exhibit appetite suppressing activity including inhibition of food intake. Smaller fragments, peptides of, for example, 3 to 13 amino acids are also contemplated by the present invention. Larger peptides of, for example, 15 to about 30 amino acids, each containing within its sequence the aforementioned repeat sequence are also contemplated by the present invention.

The term "fragment" refers to any subject peptide having an amino acid sequence which is a contiguous part of any peptide depicted in SEQ ID NOS:1–10 and which fragment retains the appetite suppressant or feeding inhibition properties as the subject peptide including SEQ ID NOS:11–87.

In one embodiment of the invention, the amino acid sequences of the eating suppressant peptide substantially correspond to amino acid residues 21–50 of the rat apolipoprotein A-IV precursor (See SEQ ID NO:1), as well as homologs, analogs and fragments thereof.

In another embodiment, the amino acid sequences of the appetite suppressant peptides substantially correspond to amino acid residues 37–50 of the rat apo A-IV precursor as well as sequence homologs, analogs and fragments thereof. See e.g., SEQ ID NO:3 and SEQ ID NO:4. By "homologs" is meant the corresponding peptides derived from other known apo A-IV proteins and having the same or substantially the same appetite suppressant and food intake inhibition properties. By "analogs" is meant substitutions in the amino acid sequences of the peptides, providing the appetite suppressant and feeding inhibition properties are retained. Analogs may also encompass additional amino acids, added to the N- and/or C-terminal portion of the peptide. For example, analogs of the peptides of the invention may contain cysteine or another amino acid, at the amino or carboxyl end of the peptide by which the peptide may be covalently attached to a carrier protein, e.g., albumin for in vivo administration. Other carrier molecules include polyethylene glycol (PEG) which functions to avoid proteolytic cleavage and clearing of peptides from the blood.

The peptides of the present invention may be linked to an additional sequence of amino acids by either or both the N-terminus and the C-terminus, wherein the additional sequences are from 1 to about 45 amino acids in length. Such additional amino acid sequences, or linker sequences can be conveniently affixed to a detectable label or solid matrix, or carrier. Labels, solid matrices and carriers that can be used with peptides of the present invention are described below. Typical amino acid residues used for linking are tyrosine, cysteine, lysine, glutamic acid and aspartic acid, or the like.

In a further embodiment, the peptides of the present invention have amino acid sequences substantially corresponding to amino acids 316–346 of the rat apolipoprotein A-IV precursor (See SEQ ID NO:7) as well as homologs, analogs and fragments thereof.

As a further aspect of the invention, there are provided peptides corresponding to the first thirty amino acids of the mature human apolipoprotein A-IV (SEQ ID NO:8) as well as homologs, analogs and fragments thereof. Also provided is a peptide corresponding to amino acid residues 37 to 50 of the human apolipoprotein A-IV precursor (SEQ ID NO:9) as well as homologs, analogs and fragments thereof. Still another embodiment of the invention is a peptide corresponding to amino acid residues 316 to 346 of the human apo A-IV precursor (SEQ ID NO:10).

In another embodiment of the invention, the appetite suppressant peptides of the present invention include specifically or substantially correspond to the following amino acid sequences:

SEQ ID NO:1 EVTSDQVANVMWDYFTQL SNNAKEAVEQLQ;
SEQ ID NO:2 EVTSDQVANVMWDYF;
SEQ ID NO:3 QLSNNNAKEAVEQLQ;
SEQ ID NO:4 QLSNNAKEAVEQLQ;
SEQ ID NO:5 TQLSNNAKEAVEQLQ;
SEQ ID NO:6 QEKLNHQMEGLAFQMKKN AEEL;
SEQ ID NO:7 ALVQQMEKFRQQLGSDSG DVESHLSFLEKN;
SEQ ID NO:8 EVSADQVATVMWDYFSQL SNNAKEAVEHLQ;
SEQ ID NO:9 QLSNNAKEAVEHLQ;
SEQ ID NO:10 ALVQQMEQLRQKLGPHAG DVEGHLSFLE;
SEQ ID NO:11 QLS
SEQ ID NO:12 NNA
SEQ ID NO:13 KEA
SEQ ID NO:14 VEQ
SEQ ID NO:15 LSN
SEQ ID NO:16 NAK
SEQ ID NO:17 EAV
SEQ ID NO:18 EQL
SEQ ID NO:19 SNN
SEQ ID NO:20 AKE
SEQ ID NO:21 AVE
SEQ ID NO:22 QLQ
SEQ ID NO:23 QLSN
SEQ ID NO:24 NAKE
SEQ ID NO:25 AVEQ
SEQ ID NO:26 LSNN
SEQ ID NO:27 AKEA
SEQ ID NO:28 VEQL
SEQ ID NO:29 SNNA
SEQ ID NO:30 KEAV
SEQ ID NO:31 EQLQ
SEQ ID NO:32 NNAK
SEQ ID NO:33 EAVE
SEQ ID NO:34 QLSNN
SEQ ID NO:35 AKEAV
SEQ ID NO:36 LSNNA
SEQ ID NO:37 KEAVE
SEQ ID NO:38 SNNAK
SEQ ID NO:39 EAVEQ
SEQ ID NO:40 NNAKE
SEQ ID NO:41 AVEQL
SEQ ID NO:42 NAKEA
SEQ ID NO:43 VEQLQ
SEQ ID NO:44 QLSNNA
SEQ ID NO:45 KEAVEQ
SEQ ID NO:46 LSNNAK
SEQ ID NO:47 EAVEQL
SEQ ID NO:48 SNNAKE
SEQ ID NO:49 AVEQLQ
SEQ ID NO:50 NNAKEA
SEQ ID NO:51 NAKEAV
SEQ ID NO:52 AKEAVE
SEQ ID NO:53 QLSNNAK
SEQ ID NO:54 EAVEQLQ
SEQ ID NO:55 LSNNAKE
SEQ ID NO:56 SNNAKEA
SEQ ID NO:57 NNAKEAV
SEQ ID NO:58 NAKEAVE
SEQ ID NO:59 AKEAVEQ
SEQ ID NO:60 KEAVEQL
SEQ ID NO:61 QLSNNAKE
SEQ ID NO:62 LSNNAKEA
SEQ ID NO:63 SNNAKEAV
SEQ ID NO:64 NNAKEAVE
SEQ ID NO:65 NAKEAVEQ
SEQ ID NO:66 AKEAVEQL
SEQ ID NO:67 KEAVEQLQ
SEQ ID NO:68 QLSNNAKEA
SEQ ID NO:69 LSNNAKEAV
SEQ ID NO:70 SNNAKEAVE
SEQ ID NO:71 NNAKEAVEQ
SEQ ID NO:72 NAKEAVEQL
SEQ ID NO:73 AKEAVEQLQ
SEQ ID NO:74 QLSNNAKEAV
SEQ ID NO:75 LSNNAKEAVE
SEQ ID NO:76 SNNAKEAVEQ
SEQ ID NO:77 NNAKEAVEQL
SEQ ID NO:78 NAKEAVEQLQ
SEQ ID NO:79 QLSNNAKEAVE
SEQ ID NO:80 LSNNAKEAVEQ
SEQ ID NO:81 SNNAKEAVEQL
SEQ ID NO:82 NNAKEAVEQLQ
SEQ ID NO:83 QLSNNAKEAVEQ
SEQ ID NO:84 LSNNAKEAVEQL
SEQ ID NO:85 SNNAKEAVEQLQ
SEQ ID NO:86 QLSNNAKEAVEQL
SEQ ID NO:87 LSNNAKEAVEQLQ

The peptides of the present invention specifically include homologs, analogs and fragments of the above-specified peptides; wherein A=Ala=Alanine
R=Arg=Arginine
N=Asn=Asparagine
D=Asp=Aspartic acid
B=Asx=Asparagine or aspartic acid
C=Cys=Cysteine
Q=Gln=Glutamine
E=Glu=Glutamic acid
Z=Glx=Glutamine or Glutamic acid
G=Gly=Glycine
H=His=Histidine
I=Ile=Isoleucine
L=Leu=Leucine
K=Lys=Lysine
F=Phe=Phenylalanine
P=Pro=Proline
S=Ser=Serine
T=Thr=Threonine
W=Trp=Tryptophan
Y=Tyr=Tyrosine
V=Val=Valine The one-letter symbols used to represent the amino acid residues in the peptides of the present invention are those symbols commonly used in the art. By "substantially corresponding" is meant an amino acid sequence having a homology to any of the listed sequences of at least about 70%.

The present invention also provides compositions for the suppression of appetite and feeding inhibition in mammals, including humans. The compositions have as their active ingredients, at least one of the above peptides according to the present invention, admixed with a physiologically acceptable carrier. The term "pharmaceutically acceptable" refers to a molecular entity or composition that does not produce an allergic or similar unwanted reaction when administered to humans.

The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (powder capsules and tablets) carriers such as starches, sugars, diluents, granulating agents, lubricants, binders, disintegrating agents and the like may be used. In addition, carriers such as liposomes, microemulsions and self emulsifiable glasses may be used.

The compositions of the present invention may also be formulated for intravenous administration. In this instance, the peptides are admixed with sterile water and saline or other pharmaceutically acceptable carrier.

The peptides of the present invention may additionally be formulated into food compositions such as nutriceuticals. By "nutriceutical" is meant any foodstuff such as, for example, liquid or powder compositions which have a pharmaceutical effect when consumed (i.e., appetite suppression or inhibition of food intake).

The peptides of the present invention may also be added, admixed, blended or otherwise incorporated with or into, e.g., powders, liquids (such as shakes), gels, gums, snackfoods, cakes, candies or other comestibles for use as food compositions or food supplements which suppress appetite or inhibit food intake.

The peptides of the present invention may be altered with modifying structures such as polyethylene glycol (PEG) to prevent proteolysis of the peptides and reduce clearing of the peptides from the blood.

These and other embodiments of the invention will be readily apparent to those of ordinary skill in view of the disclosure herein.

DETAILED DESCRIPTION OF THE DRAWING

Figure 1:
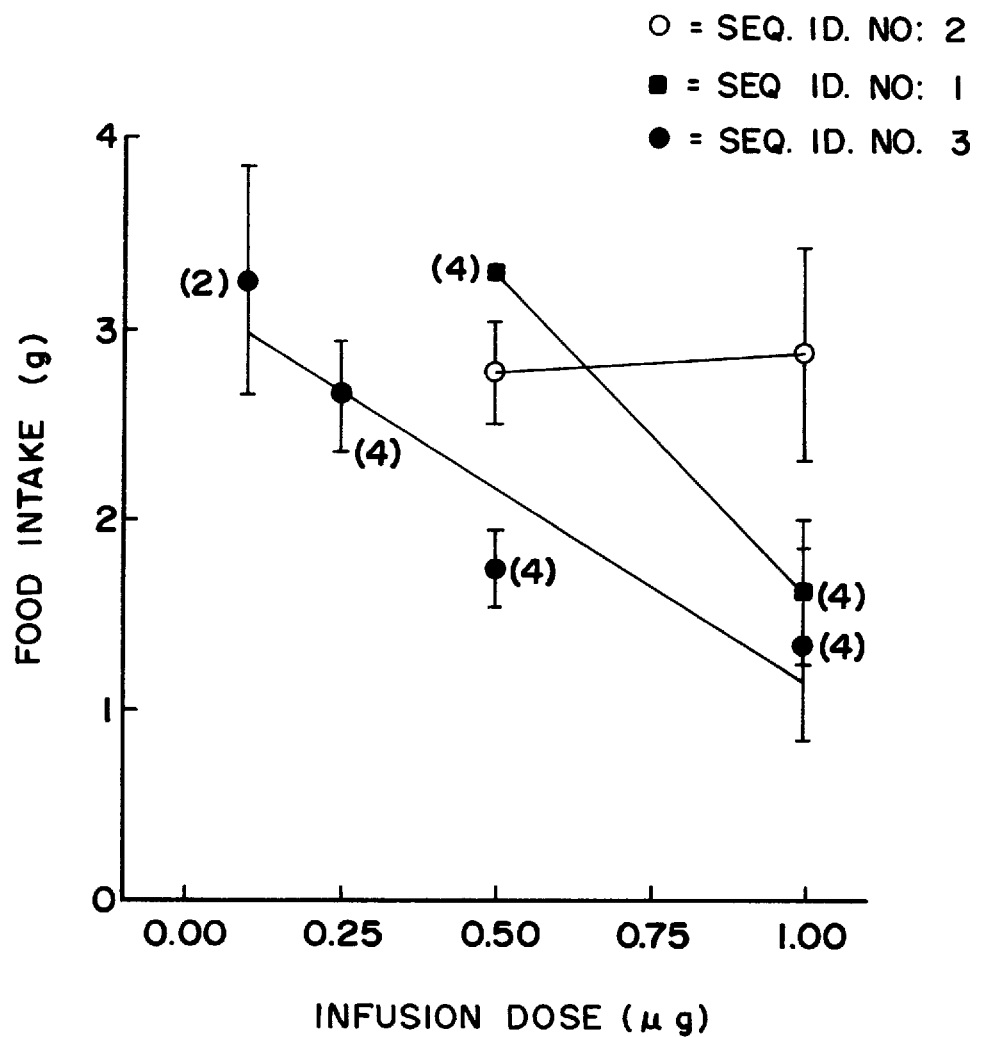
FIG. 1 is a graph comparing suppression of food intake in male Sprague Dawley rats in response to infusion of the peptides corresponding to SEQ ID NO:1, SEQ ID NO:2, and SEQ ID NO:3.
Figure 2:
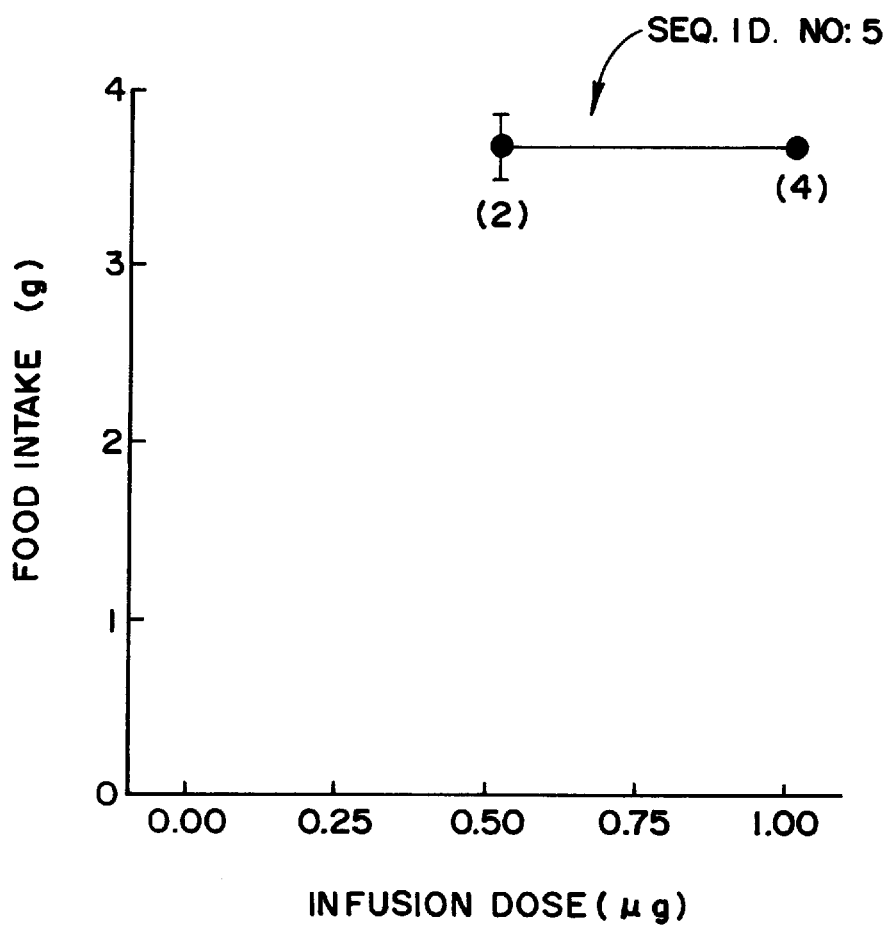
FIG. 2 is a graph demonstrating suppression of food intake in male Sprague Dawley rats in response to infusion of the peptide corresponding to SEQ ID NO:5.

The present invention provides for a number of eating suppressant peptides of, e.g., approximately 15–30 amino acids in length, including, particularly, the specified 14 amino acid peptide depicted in SEQ ID NO:4 and analogs, homologs and fragments thereof, which substantially correspond in sequence to the amino acid sequence found in specific portions of apolipoprotein A-IV. Almost all of the eating suppressant peptides of the present invention correspond to sequences found in the amino-terminal portion of apo A-IV. As used herein, "peptide" refers to a linear series of less than about 35 amino acid residues linked to one another by peptide bonds between the alpha-amino and carboxy groups of adjacent amino acid residues. The term "synthetic peptide" is intended to refer to a chemically derived chain of amino acid residues linked together by peptide bonds and which is free of naturally occurring proteins and fragments thereof. Additionally, analogs, homologs, fragments, chemical derivatives and pharmaceutically acceptable salts of the novel peptides provided herein are included within the scope of the term "peptide".

The prototype sequences of the peptides of the present invention are derived from and correspond to the amino acid sequence of rat apo A-IV; however, homologous peptides derived from human apo A-IV are also encompassed by the invention. It is known that rat and human apo A-IV are substantially homologous in amino acid sequence, with the homology being about 63%. By "homologs" is meant the corresponding peptides derived from other known apo A-IV proteins having the same or substantially the same appetite suppressant and feeding inhibition properties.

By "analogs" is meant substitutions or alterations in the amino acid sequences of the peptides of the invention, which substitutions or alterations, e.g., additions and deletions of amino acid residues, do not abolish the appetite suppressant or feeding inhibition properties of the peptides. Thus, an analog may comprise a peptide having a substantially identical amino acid sequence to a peptide provided herein as SEQ ID NOS:1–87 and in which one or more amino acid residues have been conservatively substituted with chemically similar amino acids. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated.

The phrase "conservative substitution" also includes the use of chemically derivatized residues in place of non-derivatized residues as long as the peptide retains the requisite appetite suppressant or feeding inhibition properties, which can readily be determined by the ordinarily skilled artisan. See, for example, Shargill et al., Brain Res., 544:137–140 (1991). Analogs also include the presence of additional amino acids or the deletion of one or more amino acids which do not affect biological activity. For example, analogs of the subject peptides may contain an N- or C-terminal cysteine, by which, if desired, the peptide may be covalently attached to a carrier protein, e.g., albumin. Such attachment, it is believed, will minimize clearing of the peptide from the blood and also prevent proteolysis of the peptides. In addition, for purposes of the present invention, peptides containing D-amino acids in place of L-amino acids are also included in the term "conservative substitution." The presence of such D-isomers may help minimize proteolytic activity and clearing of the peptide.

The practice of the present invention employs, unless otherwise indicated, conventional techniques of synthetic organic chemistry, protein chemistry, molecular biology, microbiology, and recombinant DNA technology, which are well within the skill of the art. Such techniques are explained fully in the literature. See e.g., Scopes, R.K., *Protein Purification Principles and Practices*, 2d ed. (Springer-Verlag. 1987), *Methods in Enzymology* (M. Deutscher, ed., Academic Press, Inc. 1990), Sambrook et al., *Molecular Cloning: A Laboratory Manual*, 2d ed., (Cold Spring Harbor Press, Cold Spring Harbor, N.Y., 1989), *Handbook of Experimental Immunology*, Vols. I-IV (D. M. Weir and C. C. Blackwell, eds., 1986, Blackwell Scientific Publications), House, *Modern Synthetic Reactions*, 2d ed., (Benjamin/ Cummings, Menlo Park, Calif., 1972).

As used herein, the term "substantially corresponds" means a peptide amino acid sequence having at least approximately 70% homology in amino acid sequence to an apolipoprotein A-IV peptide.

The term "chemical derivative" is meant to include any peptide derived from a peptide of the present invention and in which one or more amino acids have been chemically derivatized by reaction of one or more functional side groups of the amino acid residues present in the peptide. Thus, a "chemical derivative" as used herein is a peptide which is derived from the peptides identified herein by one or more chemical steps. Examples of derivatized molecules include molecules where free amino groups have been derivatized to form amine hydrochlorides, p-toluene sulfonyl groups, carbobenzoxy groups, t-butyloxycarbonyl groups, thiourethane-type derivatives, trifluroroacetyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "fragment" refers to any subject peptide having an amino acid sequence shorter than that of any peptide depicted in SEQ ID NOS:1–10 and which fragment retains the appetite suppressant or feeding inhibition properties as the subject peptides.

More specifically, the peptides of the present invention include the peptides depicted in SEQ ID NOS:11–87 which exhibit the appetite suppressant or feeding inhibition properties as SEQ ID NOS:1, 3, 4 or apo-A-IV.

The peptides of the present invention, homologs, analogs and fragments thereof may be synthesized by a number of known techniques. For example, the peptides may be prepared using the solid-phase synthetic technique initially described by Merrifield, in J. Am. Chem. Soc. 85:2149–2154(1963). Other peptide synthesis techniques may be found in M. Bodanszky et al. *Peptide Synthesis,* John Wiley & Sons, 2d Ed., (1976) and other references readily available to those skilled in the art. A summary of polypeptide synthesis techniques can be found in J. Stuart and J. D. Young, *Solid Phase Peptide Synthesis,* Pierce Chemical Company, Rockford, Ill., (1984). Peptides may also be synthesized by solution methods as described in *The Proteins,* Vol. II, 3d Ed., Neurath, H. et. al., Eds., p. 105–237, Academic Press, New York, N.Y. (1976). Appropriate protective groups for use in different peptide syntheses are described in the above-mentioned texts as well as in J. F. W. McOmie, *Protective Groups in Organic Chemistry,* Plenum Press, New York, N.Y. (1973). The peptides of the present invention might also be prepared by chemical or enzymatic cleavage from larger portions of the apolipoprotein A-IV molecule or from the entire apo A-IV molecule.

Additionally, the peptides of the present invention may also be prepared by recombinant DNA techniques. For most of the amino acids used to build proteins, more than one coding nucleotide triplet (codon) can code for a particular amino acid residue. This property of the genetic code is known as redundancy. Therefore, a number of different nucleotide sequences may code for a particular subject eating suppressant peptide. The present invention also contemplates a deoxyribonucleic acid (DNA) molecule or segment that defines a gene coding for, i.e., capable of expressing, a subject polypeptide or a subject chimeric polypeptide from which a polypeptide of the present invention may be enzymatically or chemically cleaved.

DNA molecules that encode the subject peptides can be synthesized by chemical techniques, for example, the phosphotriester method of Matteuccie et al., J. Am. Chem. Soc. 103:3185(1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are preferably chemically synthesized by the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

The preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the subject peptides include inorganic bases such as sodium hydroxide, ammonium hydroxide, potassium hydroxide and the like; and organic bases such as mono-, di-and tri-alkyl amines (e.g., triethyl amine, diisopropyl amine, methyl amine, dimethyl amine and the like) and optionally substituted ethanolamines (e.g. ethanolamine, diethanolamine and the like).

Peptide SEQ ID NOS:1–87 have the following sequences:
SEQ ID NO: 1 EVTSDQVANVMWDYFTQL SNNAKEAVEQLQ;
SEQ ID NO:2 EVTSDQVANVMWDYF;
SEQ ID NO:3 QLSNNNAKEAVEQLQ;
SEQ ID NO:4 QLSNNAKEAVEQLQ;
SEQ ID NO:5 TQLSNNAKEAVEQLQ;
SEQ ID NO:6 QEKLNHQMEGLAFQMKKN AEEL;
SEQ ID NO:7 ALVQQMEKFRQQLGSDSG DVESHLSFLEKN;
SEQ ID NO:8 EVSADQVATVMWDYFSQL SNNAKEAVEHLQ;
SEQ ID NO:9 QLSNNAKEAVEHLQ;
SEQ ID NO:10 ALVQQMEQLRQKLGPHAG DVEGHLSFLE;
SEQ ID NO:11 QLS
SEQ ID NO:12 NNA
SEQ ID NO:13 KEA
SEQ ID NO:14 VEQ
SEQ ID NO:15 LSN
SEQ ID NO:16 NAK
SEQ ID NO:17 EAV
SEQ ID NO:18 EQL
SEQ ID NO:19 SNN
SEQ ID NO:20 AKE
SEQ ID NO:21 AVE
SEQ ID NO:22 QLQ
SEQ ID NO:23 QLSN
SEQ ID NO:24 NAKE
SEQ ID NO:25 AVEQ
SEQ ID NO:26 LSNN
SEQ ID NO:27 AKEA
SEQ ID NO:28 VEQL
SEQ ID NO:29 SNNA
SEQ ID NO:30 KEAV
SEQ ID NO:31 EQLQ
SEQ ID NO:32 NNAK
SEQ ID NO:33 EAVE
SEQ ID NO:34 QLSNN
SEQ ID NO:35 AKEAV
SEQ ID NO:36 LSNNA
SEQ ID NO:37 KEAVE
SEQ ID NO:38 SNNAK
SEQ ID NO:39 EAVEQ
SEQ ID NO:40 NNAKE
SEQ ID NO:41 AVEQL
SEQ ID NO:42 NAKEA
SEQ ID NO:43 VEQLQ
SEQ ID NO:44 QLSNNA
SEQ ID NO:45 KEAVEQ
SEQ ID NO:46 LSNNAK
SEQ ID NO:47 EAVEQL
SEQ ID NO:48 SNNAKE
SEQ ID NO:49 AVEQLQ
SEQ ID NO:50 NNAKEA
SEQ ID NO:51 NAKEAV
SEQ ID NO:52 AKEAVE
SEQ ID NO:53 QLSNNAK
SEQ ID NO:54 EAVEQLQ
SEQ ID NO:55 LSNNAKE
SEQ ID NO:56 SNNAKEA
SEQ ID NO:57 NNAKEAV
SEQ ID NO:58 NAKEAVE
SEQ ID NO:59 AKEAVEQ
SEQ ID NO:60 KEAVEQL
SEQ ID NO:61 QLSNNAKE
SEQ ID NO:62 LSNNAKEA
SEQ ID NO:63 SNNAKEAV
SEQ ID NO:64 NNAKEAVE
SEQ ID NO:65 NAKEAVEQ
SEQ ID NO:66 AKEAVEQL
SEQ ID NO:67 KEAVEQLQ
SEQ ID NO:68 QLSNNAKEA
SEQ ID NO:69 LSNNAKEAV
SEQ ID NO:70 SNNAKEAVE
SEQ ID NO:71 NNAKEAVEQ
SEQ ID NO:72 NAKEAVEQL
SEQ ID NO:73 AKEAVEQLQ
SEQ ID NO:74 QLSNNAKEAV
SEQ ID NO:75 LSNNAKEAVE
SEQ ID NO:76 SNNAKEAVEQ
SEQ ID NO:77 NNAKEAVEQL
SEQ ID NO:78 NAKEAVEQLQ
SEQ ID NO:79 QLSNNAKEAVE
SEQ ID NO:80 LSNNAKEAVEQ
SEQ ID NO:81 SNNAKEAVEQL
SEQ ID NO:82 NNAKEAVEQLQ
SEQ ID NO:83 QLSNNAKEAVEQ
SEQ ID NO:84 LSNNAKEAVEQL
SEQ ID NO:85 SNNAKEAVEQLQ
SEQ ID NO:86 QLSNNAKEAVEQL
SEQ ID NO:87 LSNNAKEAVEQLQ The peptides of the present invention specifically include homologs, analogs and fragments of the above-specified peptides; wherein A=Ala=Alanine
R=Arg=Arginine
N=Asn=Asparagine
D=Asp=Aspartic acid
B=Asx=Asparagine or aspartic acid
C=Cys=Cysteine
Q=Gln=Glutamine
E=Glu=Glutamic acid
Z=Glx=Glutamine or Glutamic acid
G=Gly=Glycine
H=His=Histidine
I=Ile=Isoleucine
L=Leu=Leucine
K=Lys=Lysine F=Phe=Pheylanine
P=Pro=Proline
S=Ser=Serine
T=Thr=Threonine
W=Trp=Tryptophan
Y=Tyr=Tyrosine
v=Val=Valine Consistent with the observed properties of the peptides of the invention, the present peptides may be used as eating suppressants. In a related aspect, the present invention is also directed to methods of suppressing the appetite of animals, including humans, by administering the peptides of the present invention to the subject for a time and under conditions sufficient to achieve the desired level of appetite suppression. The peptides of the present invention are thus administered in an effective amount to suppress the appetite of the subject animal or human.

The peptides of the present invention may be administered preferably to a human patient as a pharmeceutical compositions contain a therapeutically effective dose of a least one of the peptides according to the present invention, together with a pharmaceutically acceptable carrier. The term "therapeutically effective amount" means the dose needed to produce in an individual a suppressed appetite.

Preferably, compositions containing the peptides of the present invention are administered intravenously for the purpose of suppressing food intake. There are no limitations as to the reasons behind the desired decrease in food intake. Although obese, and morbidly obese individuals are the primary targets for administration of the peptides of the present invention, it is also contemplated that other individuals with eating disorders be benefited by the peptides of the present invention. Thus, patients suffering from bulimia, anorexia nervosa or both disorders may also benefit from the effects of administering the peptides of the present invention or their antagonists.

When administered intravenously, the peptide compositions may be combined with other ingredients, such as carriers and/or adjuvants. The peptides may also be covalently attached to a protein carrier, such as albumin, so as to minimize clearing of the peptides. There are no limitations on the nature of the other ingredients, except that they must be pharmaceutically acceptable, efficacious for their intended administration and cannot degrade the activity of the active ingredients of the compositions. The peptide compositions of the invention may also be impregnated into transdermal patches or contained in subcutaneous inserts, preferably in a liquid or semi-liquid form which patch or insert time releases therapeutically effective amounts of one or more of the subject peptides.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions. Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dose of the peptide may also contain an inert diluent, as assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dose.

The precise therapeutically effective amount of peptides to be used in the methods of this invention applied to humans cannot be stated due to variations in individual eating habits and body size. In addition, a precise therapeutically effective amount of peptide is difficult to specify since it may depend on the amount of peptide which eventually arrives at the apolipoprotein A-IV receptors. However, it can generally be stated that the peptides should preferably be administered in an amount of at least about 10 mg per dose, more preferably in an amount up to about 1000 mg per dose. Since the peptide compositions of this invention will eventually be cleared from the bloodstream, re-administration of the compositions is indicated and preferred.

The peptides may be administered in a manner compatible with the dosage formulation and in such amount as will be therapeutically effective. Systemic dosages depend on the age, weight and conditions of the patient and on the administration route. For example, a suitable dose for the administration to adult humans ranges from about 1.0 to about 20 mg per kilogram of body weight.

As used herein, a pharmaceutically acceptable carrier includes any and all solvents, dispersion media, coatings, antibacterial and antifungal agents, isotonic agents and the like. The use of such media and agents are well-known in the art.

The invention is further illustrated by the following specific examples which are not intended in any way to limit the scope of the invention.

EXAMPLES

Peptide Synthesis

The peptides of the present invention were synthesized using an automatic solid phase peptide synthesizer (Milligen 9050). The synthesis was started by packing a column with a mixture of polystyrene resin (that has attached to it the C terminus amino acid of the target peptide) and glass beads (150–220 micron diameter). The amino acid bound to the resin was protected prior to packing the column and the process of peptide synthesis started by first washing the column with a 20% v/v solution of piperidine / N,N-dimethyl formamide (DMF) in order to deprotect the C terminus residue. The next residue, an FMOC protected L-amino acid (in the form of a pentafluorophenyl ester) was dissolved in a solution of hydroxybenzotriazole (HOBT/DMF) and delivered to the instrument column. In order to ensure complete coupling, the solution of amino acid/DMF was passed over the column for an extended period of 45–90 minutes. If residue attachment proved difficult due to steric reasons, the coupling time was extended by a manual modification of the instrument's built in chemical protocols. The protocol for synthesis basically consisted of a number of cycles, each one performing the following operations: deprotection of previous residue with piperidine, washing of the column with DMF, and attachment of the next residue.

After completion of the coupling reaction, the resin was washed with dichloromethane. The resin was dried and a trifluoracetic acid/phenol mixture of choice (95:5 v/v) was added to extract the peptide from the resin. If the peptide contained either methionine or cysteine residues, the cleavage of the peptide from the column was performed with a mixture of 95% Tri Floro Acetic Acid, 4% phenol and 1% of either thiophenol or anisol. The cleavage process lasts about 2–3 hours.

The supernatant was then removed by evaporation at 30–40 C. until the final volume reached approximately 2–5 milliliters. Diethyl ether was then added at this point to precipitate the peptide and the peptide was dried under a high purity, dry argon stream. The peptide was then dissolved in distilled water and freeze dried to remove phenolic compounds and remaining solvents.

Electrospray mass spectrometry was performed on each synthesized peptide and its molecular weight determined. Electrospray mass spectrometry was chosen to analyze the peptides because problems such as deletions, chemical modifications and incomplete removal of protective groups during the synthesis or cleavage/ deprotection protocols are readily detected on sample amounts as small as one picomole in a total analysis time of less than fifteen minutes. Discrepancies between the designed and actual peptide could then be determined. Where a discrepancy was detected, the peptide was sequenced using an Applied Biosystems 477A Protein Sequencer, following the manufacturer's instructions and employing routine methodologies well known to those skilled in the art.

In the amino acid sequences defined above, the numbering of the amino acid residues corresponds to the numbering of amino acid residues in the amino acid sequence for rat or human apolipoprotein A-IV as provided in Boguski et al., J. Biol. Chem., 261:6398–6407, 1986 and Karathanasis et al., Proc. Nat. Acad. Sci. USA, 83: 8457–8461, 1986, respectively. Homologous peptides are derived from the homologous regions of other apolipoprotein A-IV polypeptides, such as mouse apo A-IV, aligned in sequence for maximal homology. As noted, the apolipoprotein A-IV sequences of rat and human are about 63% homologous at the amino acid level. Human and mouse have a sequence identity of about 61% at the amino acid level.

The peptides of the present invention suppress food intake. Assays for measuring reduction in feeding can be done a number of different ways. The following experimental protocol sets forth a representative assay for measuring reduced feeding in response to administration of the peptides of the present invention.

Feeding Protocol

Animals used in vivo food intake studies were male Sprague Dawley rats weighing between 280 and 320 grams. The rats were housed in a room illuminated from 06:00 to 18:00 hours (twelve hour light-dark cycle) with a temperature maintained at 21 ±1° C. Both tap water and powdered laboratory chow (Laboratory chow #5001, Purina Mills, Inc.) were provided ad libitum to the rats.

Rats used in the study were surgically equipped with an infusion cannula in the third ventricle. Under sodium pentobarbital anesthesia (50 mg/kg ip), each rat was fixed in a stereotaxic apparatus, its skull was exposed, and two small screws were threaded into the skull to anchor the cannula. A three millimeter diameter hole was drilled in the skull on the midline six millimeters anterior to ear bar zero. A 15 mm long (23 gauge) stainless steel cannula was chronically implanted into the third ventricle, to a depth of 7.8 millimeters from the cortical surface, according to G. Paxinos and C. Watson, *The Rat Brain in Stereotaxic Coordinates*, 2d ed., (Academic Press, San Diego, 1986) Rats were allowed to recover for five days before the experiment. At testing time, food intake and body weight were ascertained to have returned to normal. All rats were handled for five minutes each day before the experiment to equilibrate their arousal levels.

In the feeding study, food was removed twenty four hours before the experiment, but free access to water was allowed. Different doses of each synthetic peptide tested were dissolved in physiological saline and infused into the third ventricle. The infusion rate was $i\mu l$/minute for ten minutes and infusions were administered under unrestrained and unanesthetized conditions beginning ten minutes before food was provided. After twenty four hours of fasting, each rat was re-fed at 13:00 hour, and powdered food consumption was measured at thirty minutes after the resumption of feeding.

As a control, 10 $\mu l$ saline (vehicle) was infused into the third ventricle and the amount of food consumed for the thirty minute period was 4.5 ±0.5 grams (Mean ±SE, N=5).

In an alternative mode of administering the peptides of the present invention, the peptide corresponding to SEQ ID NO:4 was also administered by intravenous infusion.

Data from the feeding study were evaluated using one-way analysis of variance, and multiple comparisons were carried out using the method of least significant difference. Differences were considered significant when the probability of the difference occurring by chance was less than 5 in 100 (P <0.05).

Example 1

The following 30-mer peptide corresponding to the first thirty amino acids of the mature rat apo A-IV (starting at amino acid position 21 of the apo A-IV precursor) was synthesized by solid phase peptide synthesis on a Milligen synthesizer (model 9050), analyzed by mass spectometry and washed with ether to remove phenolic compounds:

EVTSDQVANVMWDYF

TQLSNNAKEAVEQLQ (SEQ ID NO:1).

The peptide was suspended at a concentration of 100$\mu$g peptide per ml buffered solution and then tested at different doses for its ability to suppress eating in male Sprague Dawley rats. Administration of the peptide was by infusion into the third ventricle. Two groups of four rats were used in the study. Each rat in the first group received a dose of 0.50$\mu$g of peptide while each rat in the second group received a dose of 1.0 $\mu$g of peptide.

Eighteen of the thirty amino acids of the peptide corresponding to SEQ ID NO:1, beginning at the second Aspartic acid, (D), followed by Tyr and Phe ((Y and F) belong to the repeated sequence described by Boguski et al. (Proc. Natl. Acad. Sci. U.S.A. 81: 5021–5025, 1984)).

When the peptide corresponding to SEQ ID NO:1, was analyzed by mass spectometry, a problem with the incorporation of one of the amino acids was observed. Most likely, the missing amino acid is threonine and its failure to incorporate into the peptide is probably due to steric hindrance. As shown in FIG. 1, the 30-mer (probably mainly a 29-mer) corresponding to SEQ ID NO:1 proved to inhibit food intake in a dose-dependent manner.

Example 2

The following 15-mer peptide corresponding to the first fifteen amino acids of the mature rat apo A-IV (starting at position 21 of the apo A-IV precursor) was synthesized by solid phase peptide synthesis on a Milligen synthesizer (model 9050), analyzed by mass spectometry and washed with ether to remove phenolic compounds:

EVTSDQVANVMWDYF (SEQ ID NO:2).

The subject peptide was suspended at a concentration of 100 μg per ml buffered solution and then tested at different doses for its ability to suppress eating in male Sprague Dawley rats. Administration of the peptide was by infusion into the third ventricle. Two groups of rats were used in the study. The first group of four rats received 0.5μg of the peptide while the second group of four rats received 1.0μg of peptide. The last three residues of this peptide, Asp, Tyr, and Phe, (D,Y and F) represent the first three residues of the repeated sequence described by Boguski et al., (Proc. Natl. Acad. Sci. U.S.A. 81: 5021–5025, 1984). As depicted in FIG. 1, this 15-mer peptide corresponding to SEQ ID NO:2 is ineffective in inhibiting food intake.

Example 3

The following 15-mer peptide substantially corresponding to the last fifteen amino acids of the peptide of SEQ ID NO:1 (starting at position 37 of the rat apo A-IV precursor) was synthesized by solid phase peptide synthesis on a Milligen synthesizer (model 9050), analyzed by mass spectrometry and washed with ether to remove phenolic compounds:

QLSNNNAKEAVEQLQ (SEQ ID NO:3).

The peptide was suspended at a concentration of 100 μg per ml of buffered solution and then tested at different doses for its ability to suppress eating in male Sprague Dawley rats. Administration of the peptide was by infusion into the third ventricle. Four groups of rats were used in the study. Each rat in the first group of four rats received a dose of 0.25μg of peptide while each rat in the second and third group (each containing four rats) received 0.50μg or 1.00μg of peptide respectively. A fourth group of two rats received a dose of 0.125 μg of peptide.

As shown in FIG. 1, the 15-mer peptide corresponding to SEQ ID NO:3 is effective in inhibiting food intake in a dose dependent manner. The first amino acid residue in the stretch of final fifteen amino acids of SEQ ID NO:1 is Thr (T) which corresponds to position 36 of the apo A-IV precursor.

Amino acid sequencing of the resultant peptide revealed that the peptide lacked a Thr (T) at position 36 and instead contained Gln (Q) as the first amino acid in the peptide. In addition, during synthesis, an additional Asn (N) was incorporated into the peptide after the two Asn residues normally found at positions 40 and 41 of the apo A-IV precursor.

Since the peptide corresponding to SEQ ID NO:3 is effective in inhibiting food intake in a dose dependent manner as shown in FIG. 1, the deletion of Thr (T) and the addition of Asn (N) do not interfere with the biological activity of the altered peptide.

Example 4

The following 14-mer peptide corresponding to amino acids 37 to 50 of the rat apo A-IV precursor was synthesized by solid phase peptide synthesis on a Milligen synthesizer (model 9050), analyzed by mass spectometry and washed with ether to remove phenolic compounds:

QLSNNAKEAVEQLQ (SEQ ID NO:4).

Figure 3A:
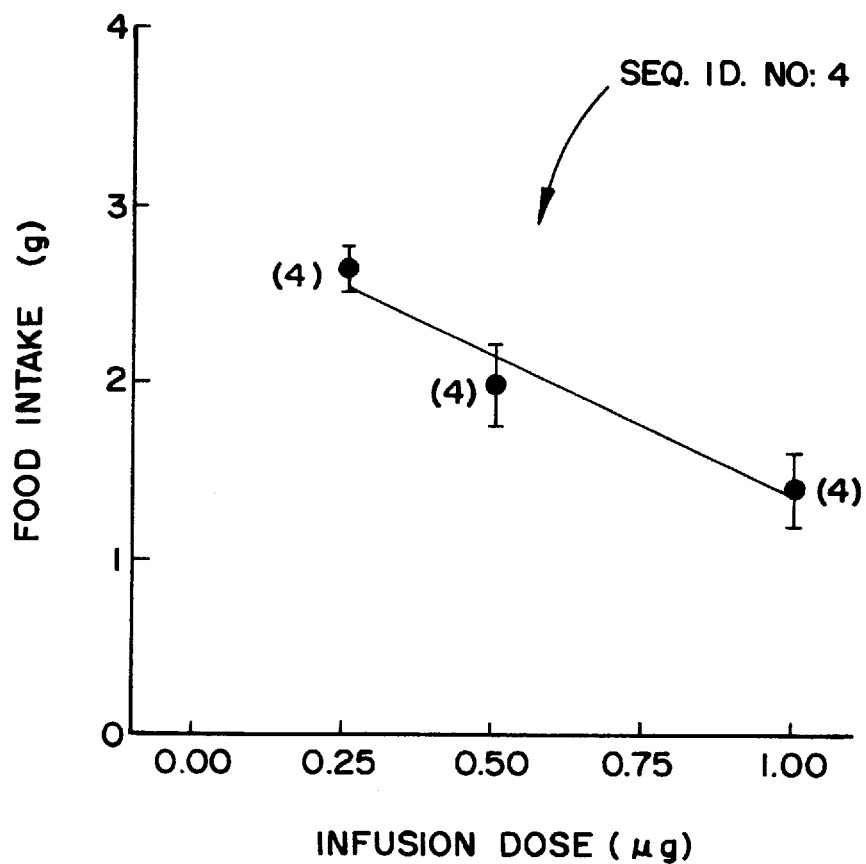
FIG. 3a is a graph demonstrating suppression of food intake in male Sprague Dawley rats in response to infusion of the peptide corresponding to SEQ ID NO:4.
Figure 3B:
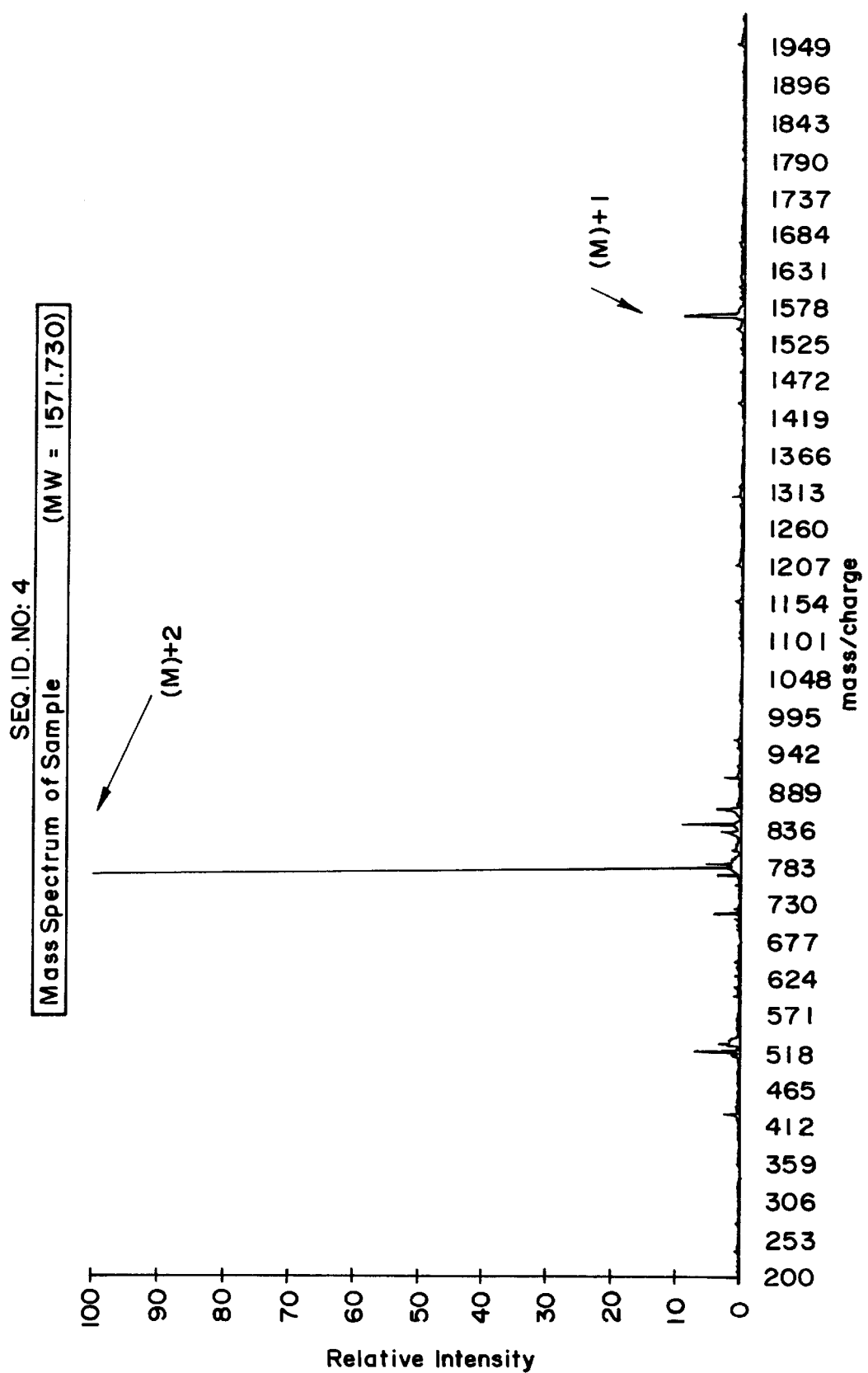
FIG. 3b is a mass spectrum of the peptide corresponding to SEQ ID NO:4.

The peptide was then suspended at a concentration of 100μg per ml of buffered solution and tested at different doses for its ability to suppress eating in male Sprague Dawley rats. Administration of the peptide was by infusion into the third ventricle. Three groups of four rats were used in the study. Each rat in the first group received a dose of 0.25μg of peptide while each rat in the second and third group received 0.5 or 1.0μg of peptide respectively. The peptide corresponding to SEQ ID NO:4 was found to be effective in inhibiting food intake in a dose dependent manner (FIG. 3a). The peptide corresponding to SEQ ID NO:4 was also found to be as effective as the peptide of SEQ ID NO:3 in inhibition of food intake. Further, both peptides corresponding to SEQ ID NO:3 and SEQ ID NO:4 are more effective at suppressing food intake than the peptide of SEQ ID NO:1 based on the dose in μg of peptide administered.

It should also be noted that when the amino acid sequence of the peptide corresponding to SEQ ID NO:4 is compared to the same region of human apo A-IV, 13 of 14 amino acids are identical. This represents a degree of homology of 93% at the amino acid sequence level.

In addition to central application via infusion of the peptide into the third ventricle, three male Sprague Dawley rats were administered 200μg of the peptide corresponding to SEQ ID NO:4 by intravenous infusion. Food intake decreased by 20–40% (20 %, 31%, and 39% respectively in three test rats) in the one hour study period. This finding demonstrates that the eating suppressant effects of the peptide corresponding to SEQ ID NO:4 and the other subject peptides are not limited to central application.

Example 5

The following 15-mer peptide corresponding to the last fifteen amino acids of the peptide of SEQ ID NO:1 (starting at position 36 of the rat apo A-IV precursor) was synthesized by solid phase peptide synthesis on a Milligen synthesizer (model 9050), analyzed by mass spectrometry and washed with ether to remove phenolic compounds:

TQLSNNAKEAVEQLQ (SEQ ID NO:5).

The peptide was suspended at a concentration of 100 μg per ml of buffered solution and then tested at different doses for its ability to suppress eating in male Sprague Dawley rats. Administration of the peptide was by infusion into the third ventricle. Two groups of rats were used in the study. A dose of 0.5μg of peptide was administered to a first group of two rats and a dose of 1.0μg peptide was administered to a second group of four rats. The peptide of SEQ ID NO:5 represents amino acid position 36–50 of the apo A-IV precursor.

Example 6

The following 22-mer peptide corresponding to amino acids 231–252 of the rat apo A-IV precursor was synthesized by solid phase peptide synthesis on a Milligen synthesizer (model 9050), analyzed by mass spectrometry and washed with ether to remove phenolic compounds:

QEKLNHQMEGL
AFQMKKNAEEL (SEQ ID NO: 6).

This peptide encompasses a stretch of amino acids having considerable homology between rat and human apo A-IV. The rat and human amino acid sequences are identical in twenty out of twenty-two positions giving an amino acid sequence homology of 90%.

Figure 4:
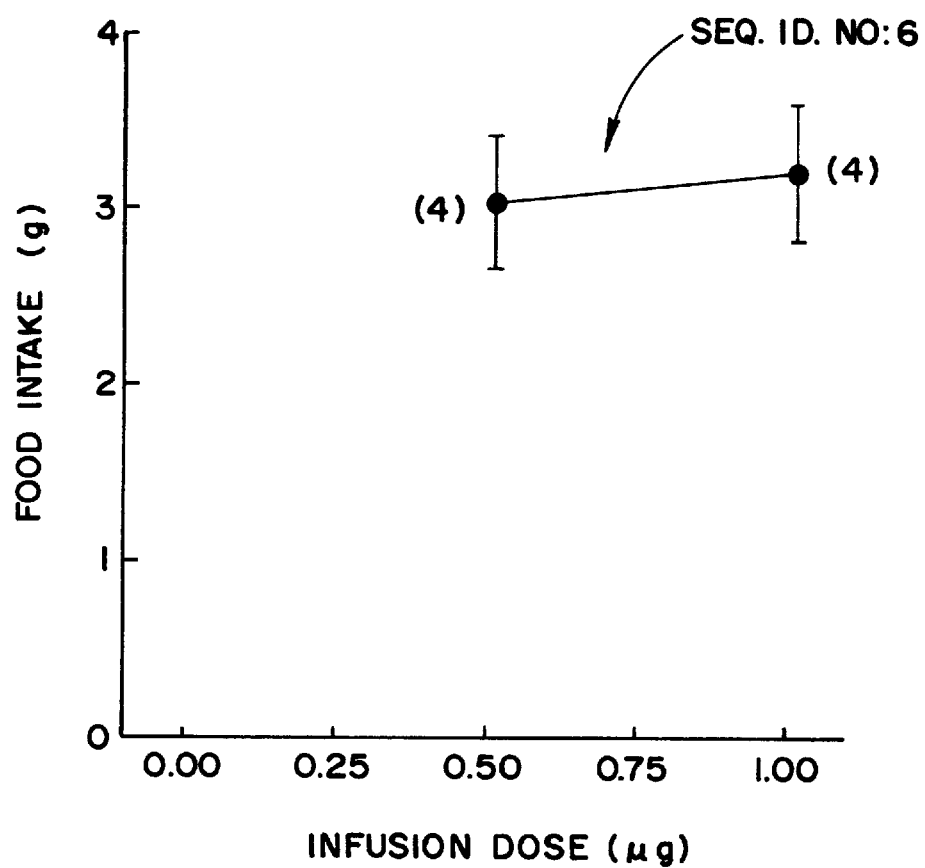
FIG. 4 is a graph demonstrating suppression of food intake in male Sprague Dawley rats in response to infusion of the peptide corresponding to SEQ ID NO:6.

The peptide was suspended at a concentration of 100μg per ml of buffered solution and then tested at different doses for its ability to suppress eating in male Sprague Dawley rats. Administration of the peptide was by infusion into the third ventricle. Two groups of four rats were used in the study. Each rat in the first group received a dose of 0.5μg of peptide while each rat in the second group received a dose of 1.0μg of the peptide. As shown in FIG. 4, neither dose showed any effect on food intake.

Example 7

The following 30-mer peptide corresponding to amino acids 316–346 of the rat apo A-IV precursor was synthesized by solid phase peptide synthesis on a Milligen synthesizer (model 9050), analyzed by mass spectrometry and washed with ether to remove phenolic compounds:

ALVQQMEKFR
QQLGSDSGDV
ESHLSFLEK N (SEQ ID NO:7).

The peptide was suspended at a concentration of 100μg per ml of buffered solution and then tested at different doses for its ability to suppress eating in male Sprague Dawley rats. Administration of the peptide was by infusion into the third ventricle. Two groups of rats were used in the study, the first group having four rats and the second group having six rats. Each rat in the first group received a dose of 0.5μg of peptide while each rat in the second group received a dose of 1.0μg of peptide.

Figure 5:
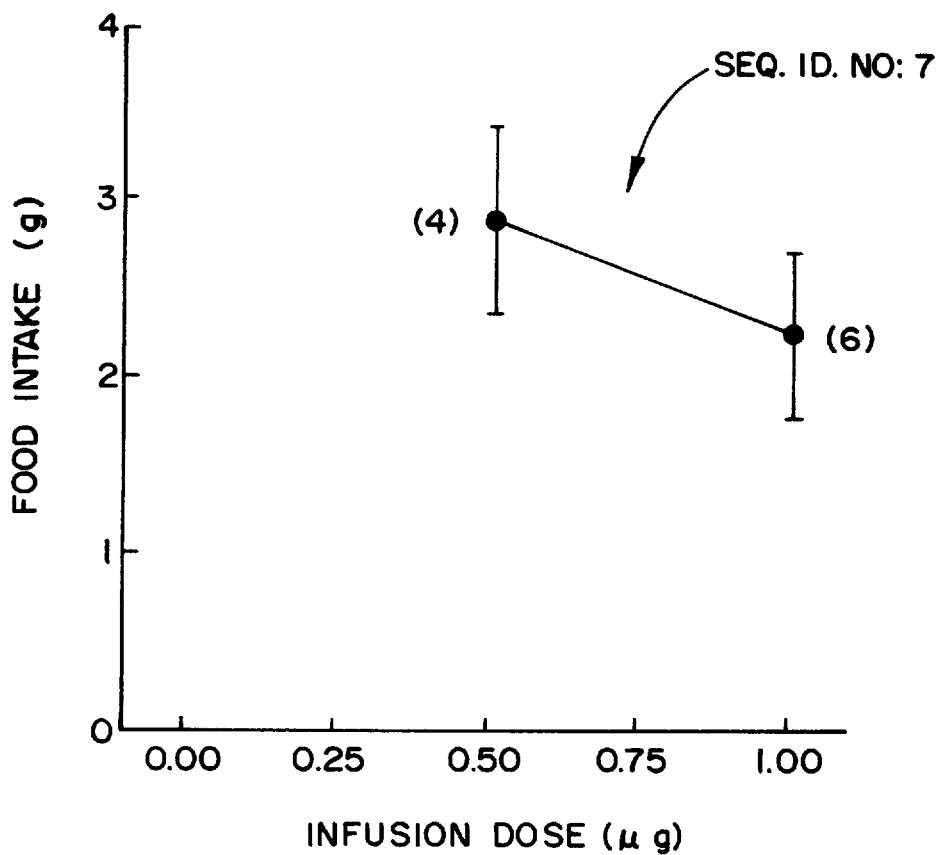
FIG. 5 is a graph demonstrating suppression of food intake in male Sprague Dawley rats in response to infusion of the peptide corresponding to SEQ ID NO:7.

As shown in FIG. 5, the peptide was found to inhibit food intake. The difference in food intake between the 0.5μg and the 1.04μg dose was not found to be statistically significant. Further, when compared to the peptides comprising SEQ ID NO:3 or SEQ ID NO:4, it was found that the peptide comprising SEQ ID NO:7 was not as effective in inhibiting food intake.

Example 8

Figure 6:
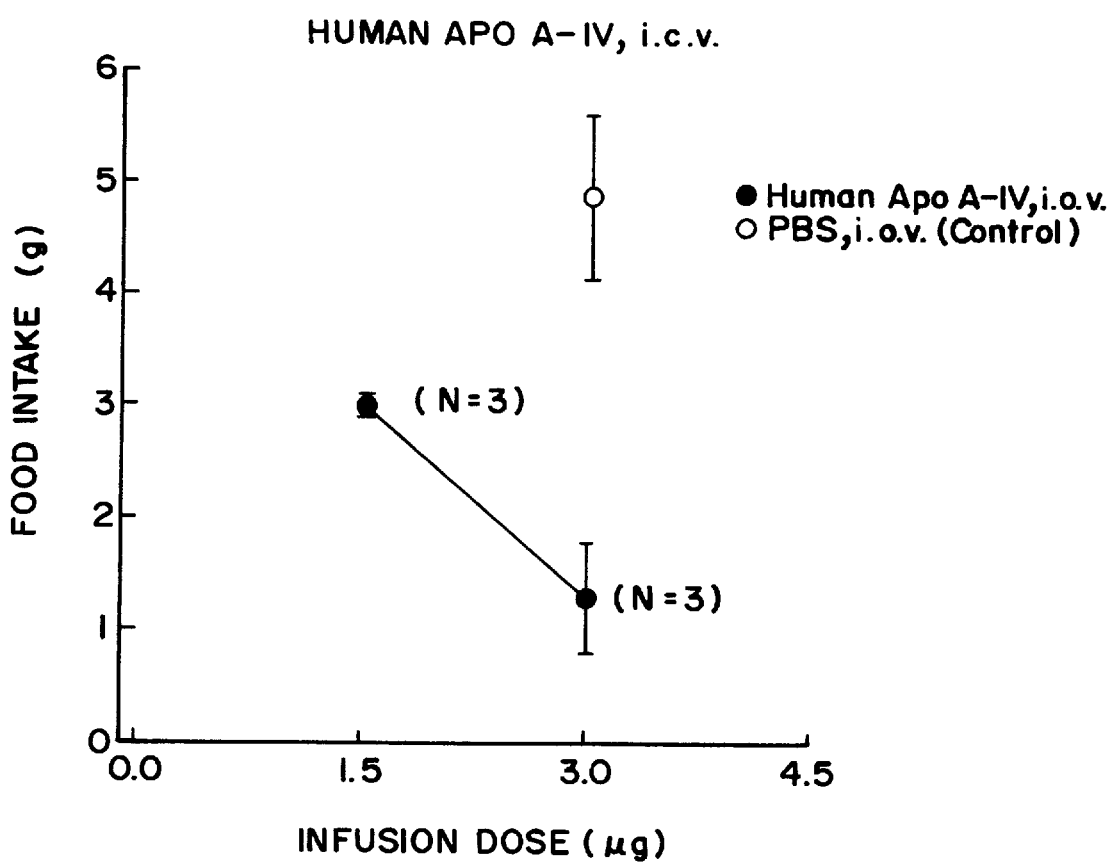
FIG. 6 is a graph demonstrating suppression of food intake in male Sprague Dawley rats in response to infusion of human apolipoprotein A-IV.

The entire human apolipoprotein A-IV molecule was obtained from human serum and purified by preparative polyacrylamide gel electrophoresis. The polypeptide was then suspended in buffered saline to a concentration of 100 μg per ml and tested for its ability to suppress food intake in male Sprague Dawley rats. The apo A-IV solution was administered to male Sprague Dawley rats by infusion into the third ventricle at a dose of 1.5 and 3 μg per rat. As depicted in FIG. 6, human apo A-IV was found to be effective in suppressing food intake in rats in a dose dependent manner. This finding establishes that human apolipoprotein A-IV has appetite suppressant properties as would be expected. Further, the different amino acid sequence of human apo A-IV does not appear to effect the appetite suppressant properties when human apo A-IV is administered to rats.

Example 9

The following 30-mer peptide corresponding to the first thirty amino acids of the mature human apolipoprotein A-IV (starting at position 21 of the apo A-IV precursor) is synthesized by solid phase peptide synthesis, analyzed by mass spectrometry and washed with ether to remove phenolic compounds:

EVSADQVATVMWDYF
SQLSNNAKEAVEHLQ (SEQ ID NO:8).

The peptide is stored as a lyophilized powder or immediately solubilized in a buffered saline solution for intravenous, oral or other formulation.

Example 10

The following 14 mer peptide corresponding to amino acids 37 to 50 of the human apo A-IV precursor is synthesized by solid phase peptide synthesis analyzed by mass spectrometry and washed with ether to remove phenolic compounds:

QLSNNAKEAVEHLQ (SEQ ID NO:9).

The peptide is stored as a lyophilized powder or immediately solubilized in a buffered saline solution for intravenous, oral or other formulation.

Example 11

The following 30-mer peptide corresponding to amino acids 316–346 of the human apo A-IV precursor is synthesized by solid phase peptide synthesis, analyzed by mass spectometry and washed with ether to remove phenolic compounds:

ALVQQMEQLRQKLGP
HAGDVEGHLSFLEKD (SEQ ID NO:10).

The peptide is stored as a lyophilized powder or immediately solubilized in a buffered saline solution or sterile water for intravenous, oral or other formulation.

What is claimed is:

1. A peptide consisting of 9 to 30 amino acids comprising 7 contiguous amino acids of SEQ ID NO:4 and analogs and homologs thereof, wherein said analogs and homologs consist of 9 to 30 amino acids and wherein said peptide, analogs and homologs suppress appetite or inhibit food intake when administered to a mammal.

2. The peptide of claim 1 wherein the peptide has the sequence of SEQ ID NO:1, and analogs and homologs of said peptide.

3. The peptide of claim 1 wherein the peptide has the sequence of SEQ ID NO:3, and analogs and homologs of said peptide.

4. The peptide of claim 1 wherein the peptide has the sequence of SEQ ID NO:4, and analogs and homologs of said peptide.

5. The peptide of claim 1 wherein the peptide has the sequence of SEQ ID NO:9, and analogs and homologs of said peptide.

6. A peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:14, SEQ ID NO:15, SEQ ID NO:16, SEQ ID NO:17, SEQ ID NO;18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO;31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO;45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86 and SEQ ID NO:87 and analogs and homologs of said peptide wherein said analogs and homologs consist of 9 to 30 amino acids and wherein said peptide, analogs and homologs suppress appetite or inhibits food intake when administered to a mammal.

7. A method of suppressing appetite and food intake in mammals comprising the administration of 5 or 6 least one of the peptides of any one of claims 2, 3, 4, in an amount effective to suppress the appetite and food intake of said mammal.

8. A method of suppressing appetite and food intake in mammals comprising the administration of the peptide of claim 1 in an amount effective to suppress the appetite and food intake of said mammal.

9. The method of claim 8 where said mammal is human.

10. A pharmaceutical composition comprising at least one peptide of any one of claims 2, 3, 4, 5, or 6 admixed with a pharmaceutically acceptable carrier.

11. A pharmaceutical composition comprising the peptide of claim 1 admixed with a pharmaceutically acceptable carrier.

12. A food composition comprising at least one peptide of any one of claims 2, 3, 4, 5, or 6.

13. A food composition comprising the peptide of claim 1.

14. A nutriceutical comprising at least one peptide of any one of claims 2, 3, 4, 5, or 6.

15. A nutriceutical comprising at the peptide of claim 1.

16. A peptide selected from the group consisting of SEQ ID NO:1, SEQ ID NO:3, SEQ ID NO:4, SEQ ID NO:7, SEQ ID NO:53, SEQ ID NO:54, SEQ ID NO:79, SEQ ID NO:80, SEQ ID NO:81, SEQ ID NO:82, SEQ ID NO:84, SEQ ID NO:86 and SEQ ID NO:87.

17. A peptide consisting of 9 to 30 amino acids comprising 7 contiguous amino acids of SEQ ID NO:7 and analogs and homologs thereof, wherein said analogs and homologs consist of 9 to 30 amino acids and wherein said peptide, analogs and homologs suppress appetite or inhibit food intake when administered to a mammal.

18. A peptide consisting of 9 to 30 amino acids comprising 7 contiguous amino acids of SEQ ID NO:10 and analogs and homologs thereof, wherein said peptide, analogs and homologs consist of 9 to 30 amino acids and suppress appetite or inhibit food intake when administered to a mammal.

* * * * *

UNITED STATES PATENT AND TRADEMARK OFFICE
CERTIFICATE OF CORRECTION

PATENT NO. : 5,840,688  
DATED : November 24, 1998  
INVENTOR(S) : Patrick Tso

Page 1 of 1

It is certified that error appears in the above-identified patent and that said Letters Patent is hereby corrected as shown below:

Column 8,  
Line 8: "DETAILED DESCRIPTION OF THE DRAWING" should read --DETAILED DESCRIPTION OF THE INVENTION--

Column 13,  
Line 1: "pheylalanine" should read --phenylalanine--  
Line 19: "...pharmaceutical compositions contain..." should read --...pharmaceutical compositions in a therapeutically effective amount.--

Column 15,  
Line 51: "in vivo" should read --in invivo--

Column 56, Claim 6:  
Line 41, After "SEQ ID NO:29", Insert --SEQ ID NO:30--

Column 57, Claim 15:  
Line 16, "comprising at the peptide" should read --comprising the peptide--

Signed and Sealed this

Seventeenth Day of July, 2001

*Attest:*

NICHOLAS P. GODICI  
*Attesting Officer*    Acting Director of the United States Patent and Trademark Office

SEQUENCE LISTING ( 1 ) GENERAL INFORMATION:

( i i i ) NUMBER OF SEQUENCES: 88

( 2 ) INFORMATION FOR SEQ ID NO:1:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Glu Val Thr Ser Asp Gln Val Ala Asn Val Met Trp Asp Tyr Phe Thr
1               5                   10                  15

Gln Leu Ser Asn Asn Ala Lys Glu Ala Val Glu Gln Leu Gln
        20                  25                  30

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Glu Val Thr Ser Asp Gln Val Ala Asn Val Met Trp Asp Tyr Phe
1               5                   10                  15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Gln Leu Ser Asn Asn Asn Ala Lys Glu Ala Val Glu Gln Leu Gln
1               5                   10                  15
```

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gln Leu Ser Asn Asn Ala Lys Glu Ala Val Glu Gln Leu Gln
1               5                   10
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Thr Gln Leu Ser Asn Asn Ala Lys Glu Ala Val Glu Gln Leu Gln
1               5                   10                  15
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gln Glu Lys Leu Asn His Gln Met Glu Gly Leu Ala Phe Gln Met Lys
1               5                   10                  15

Lys Asn Ala Glu Glu Leu
```

20

( 2 ) INFORMATION FOR SEQ ID NO:7:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala  Leu  Val  Gln  Gln  Met  Glu  Lys  Phe  Arg  Gln  Gln  Leu  Gly  Ser  Asp
1                  5                       10                      15
Ser  Gly  Asp  Val  Glu  Ser  His  Leu  Ser  Phe  Leu  Glu  Lys  Asn
                20                  25                      30
```

( 2 ) INFORMATION FOR SEQ ID NO:8:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Glu  Val  Ser  Ala  Asp  Gln  Val  Ala  Thr  Val  Met  Trp  Asp  Tyr  Phe  Ser
1                  5                       10                      15
Gln  Leu  Ser  Asn  Asn  Ala  Lys  Glu  Ala  Val  Glu  His  Leu  Gln
                20                  25                      30
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gln  Leu  Ser  Asn  Asn  Ala  Lys  Glu  Ala  Val  Glu  His  Leu  Gln
1                  5                       10
```

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Ala  Leu  Val  Gln  Gln  Met  Glu  Gln  Leu  Arg  Gln  Lys  Leu  Gly  Pro  His
1                  5                       10                      15
Ala  Gly  Asp  Val  Glu  Gly  His  Leu  Ser  Phe  Leu  Glu
                20                  25
```

( 2 ) INFORMATION FOR SEQ ID NO:11:

( i ) SEQUENCE CHARACTERISTICS:
        ( A ) LENGTH: 3 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Gln Leu Ser
1

( 2 ) INFORMATION FOR SEQ ID NO:12:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Asn Asn Ala
1

( 2 ) INFORMATION FOR SEQ ID NO:13:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Lys Glu Ala
1

( 2 ) INFORMATION FOR SEQ ID NO:14:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Val Glu Gln
1

( 2 ) INFORMATION FOR SEQ ID NO:15:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Leu Ser Asn
1

( 2 ) INFORMATION FOR SEQ ID NO:16:

( i ) SEQUENCE CHARACTERISTICS:
( A ) LENGTH: 3 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:16:

Asn Ala Lys
1

(2) INFORMATION FOR SEQ ID NO:17:

(i) SEQUENCE CHARACTERISTICS:
(A) LENGTH: 3 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:17:

Glu Ala Val
1

(2) INFORMATION FOR SEQ ID NO:18:

(i) SEQUENCE CHARACTERISTICS:
(A) LENGTH: 3 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:18:

Glu Gln Leu
1

(2) INFORMATION FOR SEQ ID NO:19:

(i) SEQUENCE CHARACTERISTICS:
(A) LENGTH: 3 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:19:

Ser Asn Asn
1

(2) INFORMATION FOR SEQ ID NO:20:

(i) SEQUENCE CHARACTERISTICS:
(A) LENGTH: 3 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:20:

Ala Lys Glu
1

(2) INFORMATION FOR SEQ ID NO:21:

(i) SEQUENCE CHARACTERISTICS:
(A) LENGTH: 3 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Ala Val Glu
    1

(2) INFORMATION FOR SEQ ID NO:22:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Gln Leu Gln
    1

(2) INFORMATION FOR SEQ ID NO:23:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Gln Leu Ser Asn
    1

(2) INFORMATION FOR SEQ ID NO:24:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Asn Ala Lys Glu
    1

(2) INFORMATION FOR SEQ ID NO:25:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Ala Val Glu Gln
    1

(2) INFORMATION FOR SEQ ID NO:26:

(i) SEQUENCE CHARACTERISTICS:
            (A) LENGTH: 4 amino acids (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:26:

Leu  Ser  Asn  Asn
        1

(2) INFORMATION FOR SEQ ID NO:27:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:27:

Ala  Lys  Glu  Ala
        1

(2) INFORMATION FOR SEQ ID NO:28:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:28:

Val  Glu  Gln  Leu
        1

(2) INFORMATION FOR SEQ ID NO:29:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:29:

Ser  Asn  Asn  Ala
        1

(2) INFORMATION FOR SEQ ID NO:30:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:30:

Lys  Glu  Ala  Val
        1

(2) INFORMATION FOR SEQ ID NO:31:

(i) SEQUENCE CHARACTERISTICS:
                (A) LENGTH: 4 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

Glu Gln Leu Gln
1

(2) INFORMATION FOR SEQ ID NO:32:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

Asn Asn Ala Lys
1

(2) INFORMATION FOR SEQ ID NO:33:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

Glu Ala Val Glu
1

(2) INFORMATION FOR SEQ ID NO:34:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Gln Leu Ser Asn Asn
1               5

(2) INFORMATION FOR SEQ ID NO:35:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:35:

Ala Lys Glu Ala Val
1               5

(2) INFORMATION FOR SEQ ID NO:36:

(i) SEQUENCE CHARACTERISTICS:
(A) LENGTH: 5 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

Leu Ser Asn Asn Ala
1               5

( 2 ) INFORMATION FOR SEQ ID NO:37:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

Lys Glu Ala Val Glu
1               5

( 2 ) INFORMATION FOR SEQ ID NO:38:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Ser Asn Asn Ala Lys
1               5

( 2 ) INFORMATION FOR SEQ ID NO:39:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

Glu Ala Val Glu Gln
1               5

( 2 ) INFORMATION FOR SEQ ID NO:40:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:40:

Asn Asn Ala Lys Glu
1               5

( 2 ) INFORMATION FOR SEQ ID NO:41:

( i ) SEQUENCE CHARACTERISTICS:
( A ) LENGTH: 5 amino acids ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:41:

Ala  Val  Glu  Gln  Leu
    1                   5

( 2 ) INFORMATION FOR SEQ ID NO:42:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:42:

Asn  Ala  Lys  Glu  Ala
    1                   5

( 2 ) INFORMATION FOR SEQ ID NO:43:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:43:

Val  Glu  Gln  Leu  Gln
    1                   5

( 2 ) INFORMATION FOR SEQ ID NO:44:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:44:

Gln  Leu  Ser  Asn  Asn  Ala
    1                   5

( 2 ) INFORMATION FOR SEQ ID NO:45:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:45:

Lys  Glu  Ala  Val  Glu  Gln
    1                   5

( 2 ) INFORMATION FOR SEQ ID NO:46:

( i ) SEQUENCE CHARACTERISTICS:
            ( A ) LENGTH: 6 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:46:

Leu  Ser  Asn  Asn  Ala  Lys
1                      5

(2) INFORMATION FOR SEQ ID NO:47:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:47:

Glu  Ala  Val  Glu  Gln  Leu
1                      5

(2) INFORMATION FOR SEQ ID NO:48:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:48:

Ser  Asn  Asn  Ala  Lys  Glu
1                      5

(2) INFORMATION FOR SEQ ID NO:49:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:49:

Ala  Val  Glu  Gln  Leu  Gln
1                      5

(2) INFORMATION FOR SEQ ID NO:50:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:50:

Asn  Asn  Ala  Lys  Glu  Ala
1                      5

(2) INFORMATION FOR SEQ ID NO:51:

(i) SEQUENCE CHARACTERISTICS:
    (A) LENGTH: 6 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:51:

Asn Ala Lys Glu Ala Val
1               5

(2) INFORMATION FOR SEQ ID NO:52:

(i) SEQUENCE CHARACTERISTICS:
  (A) LENGTH: 6 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:52:

Ala Lys Glu Ala Val Glu
1               5

(2) INFORMATION FOR SEQ ID NO:53:

(i) SEQUENCE CHARACTERISTICS:
  (A) LENGTH: 7 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:53:

Gln Leu Ser Asn Asn Ala Lys
1               5

(2) INFORMATION FOR SEQ ID NO:54:

(i) SEQUENCE CHARACTERISTICS:
  (A) LENGTH: 7 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:54:

Glu Ala Val Glu Gln Leu Gln
1               5

(2) INFORMATION FOR SEQ ID NO:55:

(i) SEQUENCE CHARACTERISTICS:
  (A) LENGTH: 7 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:55:

Leu Ser Asn Asn Ala Lys Glu
1               5

(2) INFORMATION FOR SEQ ID NO:56:

(i) SEQUENCE CHARACTERISTICS:
  (A) LENGTH: 7 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:56:

Ser Asn Asn Ala Lys Glu Ala
1               5

(2) INFORMATION FOR SEQ ID NO:57:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:57:

Asn Asn Ala Lys Glu Ala Val
1               5

(2) INFORMATION FOR SEQ ID NO:58:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:58:

Asn Ala Lys Glu Ala Val Glu
1               5

(2) INFORMATION FOR SEQ ID NO:59:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:59:

Ala Lys Glu Ala Val Glu Gln
1               5

(2) INFORMATION FOR SEQ ID NO:60:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:60:

Lys Glu Ala Val Glu Gln Leu
1               5

(2) INFORMATION FOR SEQ ID NO:61:

(i) SEQUENCE CHARACTERISTICS:
(A) LENGTH: 8 amino acids ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:61:

Gln Leu Ser Asn Asn Ala Lys Glu
    1               5

( 2 ) INFORMATION FOR SEQ ID NO:62:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:62:

Leu Ser Asn Asn Ala Lys Glu Ala
    1               5

( 2 ) INFORMATION FOR SEQ ID NO:63:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:63:

Ser Asn Asn Ala Lys Glu Ala Val
    1               5

( 2 ) INFORMATION FOR SEQ ID NO:64:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:64:

Asn Asn Ala Lys Glu Ala Val Glu
    1               5

( 2 ) INFORMATION FOR SEQ ID NO:65:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:65:

Asn Ala Lys Glu Ala Val Glu Gln
    1               5

( 2 ) INFORMATION FOR SEQ ID NO:66:

( i ) SEQUENCE CHARACTERISTICS:
            ( A ) LENGTH: 8 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:66:

Ala Lys Glu Ala Val Glu Gln Leu
1               5

(2) INFORMATION FOR SEQ ID NO:67:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:67:

Lys Glu Ala Val Glu Gln Leu Gln
1               5

(2) INFORMATION FOR SEQ ID NO:68:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:68:

Gln Leu Ser Asn Asn Ala Lys Glu Ala
1               5

(2) INFORMATION FOR SEQ ID NO:69:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:69:

Leu Ser Asn Asn Ala Lys Glu Ala Val
1               5

(2) INFORMATION FOR SEQ ID NO:70:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:70:

Ser Asn Asn Ala Lys Glu Ala Val Glu
1               5

(2) INFORMATION FOR SEQ ID NO:71:

(i) SEQUENCE CHARACTERISTICS:
    (A) LENGTH: 9 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:71:

```
Asn Asn Ala Lys Glu Ala Val Glu Gln
1               5
```

(2) INFORMATION FOR SEQ ID NO:72:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:72:

```
Asn Ala Lys Glu Ala Val Glu Gln Leu
1               5
```

(2) INFORMATION FOR SEQ ID NO:73:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:73:

```
Ala Lys Glu Ala Val Glu Gln Leu Gln
1               5
```

(2) INFORMATION FOR SEQ ID NO:74:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:74:

```
Gln Leu Ser Asn Asn Ala Lys Glu Ala Val
1               5                   10
```

(2) INFORMATION FOR SEQ ID NO:75:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:75:

```
Leu Ser Asn Asn Ala Lys Glu Ala Val Glu
1               5                   10
```

(2) INFORMATION FOR SEQ ID NO:76:

(i) SEQUENCE CHARACTERISTICS:
(A) LENGTH: 10 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:76:

```
Ser  Asn  Asn  Ala  Lys  Glu  Ala  Val  Glu  Gln
1                   5                        10
```

(2) INFORMATION FOR SEQ ID NO:77:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Asn  Asn  Ala  Lys  Glu  Ala  Val  Glu  Gln  Leu
1                   5                        10
```

(2) INFORMATION FOR SEQ ID NO:78:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Asn  Ala  Lys  Glu  Ala  Val  Glu  Gln  Leu  Gln
1                   5                        10
```

(2) INFORMATION FOR SEQ ID NO:79:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

```
Gln  Leu  Ser  Asn  Asn  Ala  Lys  Glu  Ala  Val  Glu
1                   5                        10
```

(2) INFORMATION FOR SEQ ID NO:80:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

```
Leu  Ser  Asn  Asn  Ala  Lys  Glu  Ala  Val  Glu  Gln
1                   5                        10
```

(2) INFORMATION FOR SEQ ID NO:81:

(i) SEQUENCE CHARACTERISTICS:
        (A) LENGTH: 11 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:81:

```
Ser  Asn  Asn  Ala  Lys  Glu  Ala  Val  Glu  Gln  Leu
1                   5                        10
```

(2) INFORMATION FOR SEQ ID NO:82:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:82:

```
Asn  Asn  Ala  Lys  Glu  Ala  Val  Glu  Gln  Leu  Gln
1                   5                        10
```

(2) INFORMATION FOR SEQ ID NO:83:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:83:

```
Gln  Leu  Ser  Asn  Asn  Ala  Lys  Glu  Ala  Val  Glu  Gln
1                   5                        10
```

(2) INFORMATION FOR SEQ ID NO:84:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:84:

```
Leu  Ser  Asn  Asn  Ala  Lys  Glu  Ala  Val  Glu  Gln  Leu
1                   5                        10
```

(2) INFORMATION FOR SEQ ID NO:85:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:85:

```
Ser  Asn  Asn  Ala  Lys  Glu  Ala  Val  Glu  Gln  Leu  Gln
1                   5                        10
```

(2) INFORMATION FOR SEQ ID NO:86:

(i) SEQUENCE CHARACTERISTICS:
(A) LENGTH: 13 amino acids

-continued

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

Gln Leu Ser Asn Asn Ala Lys Glu Ala Val Glu Gln Leu
1               5                   10

(2) INFORMATION FOR SEQ ID NO:87:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

Leu Ser Asn Asn Ala Lys Glu Ala Val Glu Gln Leu Gln
1               5                   10

(2) INFORMATION FOR SEQ ID NO:88:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

Asp Tyr Phe Thr Gln Leu Ser Asn Asn Ala Lys Glu Ala Val Glu Gln
1               5                   10                  15

Leu Gln Lys Thr Asp Val
                20
```